United States Patent
Sailor et al.

(10) Patent No.: US 7,042,570 B2
(45) Date of Patent: May 9, 2006

(54) POROUS THIN FILM TIME-VARYING REFLECTIVITY ANALYSIS OF SAMPLES

(75) Inventors: Michael J. Sailor, La Jolla, CA (US); Sonia Letant, Livermore, CA (US)

(73) Assignee: The Regents of the University of California, Oakland, CA (US)

(*) Notice: Subject to any disclaimer, the term of this patent is extended or adjusted under 35 U.S.C. 154(b) by 373 days.

(21) Appl. No.: 10/339,163

(22) Filed: Jan. 9, 2003

(65) Prior Publication Data

US 2003/0146109 A1   Aug. 7, 2003

Related U.S. Application Data

(60) Provisional application No. 60/351,993, filed on Jan. 25, 2002.

(51) Int. Cl.
*G01N 21/55* (2006.01)
*C12M 1/34* (2006.01)

(52) U.S. Cl. .................................... 356/445; 435/287.1

(58) Field of Classification Search ......... 356/445–448, 356/345, 352; 385/12, 129, 130; 435/287.1, 435/287.2, 287.3, 288.7, 7.1, 808, 973; 436/164–165, 436/518, 524, 527, 805
See application file for complete search history.

(56) References Cited

U.S. PATENT DOCUMENTS

| | | | | |
|---|---|---|---|---|
| 5,212,099 A | * | 5/1993 | Marcus | 436/172 |
| 5,318,676 A | | 6/1994 | Sailor et al. | |
| 5,327,225 A | * | 7/1994 | Bender et al. | 356/445 |
| 5,338,415 A | * | 8/1994 | Sailor et al. | 205/645 |
| 5,526,120 A | * | 6/1996 | Jina et al. | 356/446 |
| 5,563,707 A | * | 10/1996 | Prass et al. | 356/517 |
| 6,130,748 A | * | 10/2000 | Kruger et al. | 356/450 |
| 6,248,539 B1 | | 6/2001 | Ghadiri et al. | |
| 6,435,008 B1 | * | 8/2002 | Baklanov et al. | 73/38 |
| 6,574,425 B1 | * | 6/2003 | Weiss et al. | 250/214 B |
| 2003/0107740 A1 | * | 6/2003 | Kaylor et al. | 356/445 |

OTHER PUBLICATIONS

"Molecular Identification by Time–Resolved Interferometry in a Porous Silicon Film", Sonia E. Letant, and Michael J. Sailor, Adv. Mater., vol. 13, No. 5., Mar. 2, 2001, pp. 335–338.

"Investigation of Porous Silicon for Vapor Sensing", Anderson, R.C.; Muller, R.S.; Tobias, C.W., *Sensors and Actuators* 1990, A21–A23, pp. 835–839.

"Porous Silicon as a Material in Microsensor Technology", Barret, S.; Gaspard, F.; Herino, R.; Ligeon, M.; Muller, F.; Ronga, I. *Sensors and Actuators A* 1992, 33, pp. 19–24.

"Proton Gated Emission from Porous Silicon", Chun, J.K.M.; Bocarsly, A. B.; Cottrell, T.R.; Benziger, J.B.; Yee, J.C. *J. Am. Chem. Soc.*, vol. 115, 1993, pp. 3024–3025.

"Surface reactivity of luminescent porous silicon", Coffer, J.L.; Lilley, S.C.; Martin, R.A.; Files–Sesler, L.A., *J. Appl. Phys.*, vol. 74, 1993, pp. 2094–2096.

"Reversible Luminescence Quenching of Porous Si by Solvents", Lauerhaas, J.M.; Credo, G.M.; Heinrich, J.L.; Sailor, M.J., *J. Am. Chem. Soc.* 1992, 114, pp. 1911–1912.

"Chemical Modification of the Photoluminescence Quenching of Porous Silicon", Lauerhaas, J.M.; Sailor, M.J., *Science* 1993, 261, pp. 1567–1568.

(Continued)

*Primary Examiner*—Michael P. Stafira
(74) *Attorney, Agent, or Firm*—Greer, Burns & Crain, Ltd.

(57) ABSTRACT

A method for analyzing gaseous or liquid samples is provided. Samples are interacted with pores of a porous thin film. A time-varying response of reflectivity is obtained from the surface of the porous thin film during the interaction. One or more analytes forming the sample or a part of the sample are identified based upon the time-varying response.

56 Claims, 5 Drawing Sheets

OTHER PUBLICATIONS

"Chemical Modification of the Porous Silicon Surface", LEE, E.J.; Ha, J.S.; Sailor, M.J., Mat. Res. Soc. Symp. Proc. 1995, 358, pp. 387–392.

"Photoderivatization of the Surface of Luminescent Porous Silicon With Formic Acid", Lee, E.J.; Ha, J.S.; Sailor, M.J.; *J. Am. Chem. Soc*. 1995, 117, pp. 8295–8296.

"Light–Induced Reactions of Porous and Single–Crystal Si Surfaces with Carboxylic Acids", Lee, E.J.; Bitner, T.W.; Ha, J.S.; Shange, M.J.; Sailor, M.J., *J. Am.Chem.Soc*. 1996, 118, pp. 5375–5382.

"Photoinduced Surface Reactions of Reverse–Biased n–type Porous Si", Lee, E.J.; Bitner T.W.; Hall, A.P.; Sailor, M.J.; *J. Vac. Sci. Technol. B* 1996, 14, pp. 2850–2854.

"Photolithographic Fabrication of Micron–Dimension Porous Si Structures Exhibiting Visible Luminescence", Doan, V.V.; Sailor, M.J., *Appl. Phys. Lett.* 1992, 60, 619–620.

"Luminescent Color Image Generation on Porous Silicon" Doan, V.V.; Sailor, M.J., *Science* 1992, 265, 1791–1792.

"Enhanced Luminescence and Optical Cavity Modes from Uniformly Etched Porous Silicon", Doan, V.V.; Curtis, C.L.; Credo, G.M.; Sailor, M.J., Mat. Res. Soc. Symp. Proc. 1993, 298, pp. 185–191.

Rosi, B., Optics; Addison–Wesley: Reading, MA 1957, pp. 125.

* cited by examiner

POROUS THIN FILM TIME-VARYING REFLECTIVITY ANALYSIS OF SAMPLES

RELATED APPLICATION REFERENCE AND PRIORITY CLAIM

This application claims priority of U.S. Provisional Application Ser. No. 60/351,993, filed Jan. 25, 2002, under 35 U.S.C. § 119.

STATEMENT OF GOVERNMENT INTEREST

This invention was made with Government assistance under NSF Grant No. DMR-9700202 and DARPA (SPAWAR) Grant No. N66001-98-C-8514. The Government has certain rights in this invention.

FIELD OF THE INVENTION

A field of the invention is sample analysis. The invention concerns other more particular fields, including but not limited to, solid state sensors, molecular identification, image analysis, and detection of gases and liquids, e.g., toxic gases, solvents, nucleic acids, and proteins.

BACKGROUND OF THE INVENTION

Sample identification is important to many commercial industries. The ability to quickly, cheaply, and accurately determine an unknown sample is important in diverse applications ranging from drug discovery to alarm systems. Scientific researchers also make use of sample analysis, for example to conduct genetic research, analyze pollutants in the atmosphere and to monitor processes, such as vapor deposition processes. Scientific researchers and commercial industries continue to find needs for sample identification and analysis.

The intensity of a porous thin film's, e.g., porous silicon, visible photoluminescence changes depending upon the types of gases absorbed to its surface. This phenomenon constitutes the basis for a simple and inexpensive chemical sensor device (See, U.S. Pat. No. 5,338,415). Methods exist to chemically alter porous silicon's surface, and porous silicon can be tuned to be sensitive for specific gases and liquids. Also see, e.g., "Investigation of Porous Si for Vapor Sensing" Anderson, R. C.; Muller, R. S.; Tobias, C. W., Sensors and Actuators 1990, A21–A23, 835–839; "Porous Silicon as a Material in Microsensor Technology" Barret, S.; Gaspard, F.; Herino, R.; Ligeon, M.; Muller, F.; Ronga, I. Sensors and Actuators A 1992, 33, 19–24; and "Proton Gated Emission from Porous Silicon" Chun, J. K. M.; Bocarsly, A. B.; Cottrell, T. R.; Benziger, J. B.; Yee, J. C. J. Am. Chem. Soc. 1993, 115, 3024–3025. Porous silicon thin film's, e.g., porous silicon, insulator and semiconductor films, can be fabricated to display well-resolved Fabry-Pérot fringes in their luminescence and reflection spectra. Such interference-based spectra are sensitive to gases or liquids adsorbed to the inner surfaces of the porous Si layer. U.S. Pat. No. 5,318,676 uses the interference based spectra to identify adsorbed individual gases or liquids. U.S. Pat. No. 6,248,539 used a binder to bind analytes in pores and then identify the analytes by detecting a shift in the reflection spectra.

There continues to be a need for fast, sensitive and inexpensive sample analysis devices. A particular need exists for devices capable of detecting constituents in liquid and gas mixtures.

SUMMARY OF THE INVENTION

A method for analyzing gaseous or liquid samples is provided. Samples are interacted with pores of a porous thin film. A time-varying response of reflectivity is obtained from the surface of the porous thin film during the interaction. One or more analytes forming the sample or a part of the sample are identified based upon the time-varying response.

DETAILED DESCRIPTION OF THE PREFERRED EMBODIMENTS

The invention is directed to the use of a porous thin film to obtain time-resolved reflectivity data and use the data to analyze a sample that is interacted with the porous thin film. The sample may be a liquid or a gas. The porous thin film is structured to have a pore size and thickness that will cause a liquid sample to diffuse in a characteristic manner that can be identified through reflectivity data obtained from the porous thin film. Thin porous films may also be tailored such that a gas sample will similarly condense in a characteristic manner that can be identified through time dependent reflectivity data obtained from the porous thin film. The data is obtained over time, i.e., at multiple times or continuously over a time period, during a period when reflectivity is changing. This occurs, for example, when a sample is first brought into contact with the porous thin film and prior to a time when the reflectivity reaches a steady state. If reflectivity is in a steady state, a state for obtaining the necessary time-varying data can be induced. It can be induced, for example, if the temperature of the porous thin film is intentionally changed. Mixture compositions having multiple analytes may be analyzed with embodiments of the invention. Pressure changes in a gas being monitored with a device of the invention may also be detected, as pressure change induces a change in reflectivity from a steady state.

Preferred embodiment sample analysis devices of the invention include a porous film, a chamber, an illumination source, a light sensor, and a controller. An analysis by a device of the invention or using the method of the invention may be conducted in real time at room temperature. Devices of the invention may be portable, and constructed from inexpensive components, e.g., porous silicon thin films, glass chambers, a tungsten lamp or LED and a CCD (charge-coupled device) or phototransistor sensor. Accordingly, the invention may be used in controlled settings, such as laboratories, as well as in field settings, such as in an industrial settings and even military settings. Reflectivity spectra may be in the visible range and beyond, e.g., near infrared. This permits illumination and sensing through media that may be a barrier in the visible range. The invention accordingly has a diverse range of applicability. Example applications include identification of biological molecules, e.g., nucleic acids and proteins, and the detection of gases, e.g., dangerous gases in an industrial setting. Other applications include detection of warfare agents and industrial solvents or fuels. Preferred embodiments of the invention use porous silicon thin films. Porous silicon is a high surface area network of silicon nanocrystallites. It can be synthesized directly from the same type of inexpensive silicon wafers that are used in the fabrication of microchips.

Its open porosity and its high surface area make it an ideal adsorbent for a variety of molecules. Porous silicon films can be prepared with pore sizes ranging from a few nanometers to several microns in diameter to allow detection of a range of analytes from small molecules to whole cells. This forms the basis for a simple and sensitive analysis device suitable for the aforementioned applications and for others such as biological molecule sensing, gene sequencing, pathogen detection, etc.

The invention will now be illustrated with respect to preferred embodiments and experimental data. In describing the invention, particular exemplary devices, formation processes, and device applications will be used for purposes of illustration. The particular embodiments and data will be understood by artisans to illustrate broader aspects of the invention, and not to limit the invention to the preferred embodiments.

Figure 1:
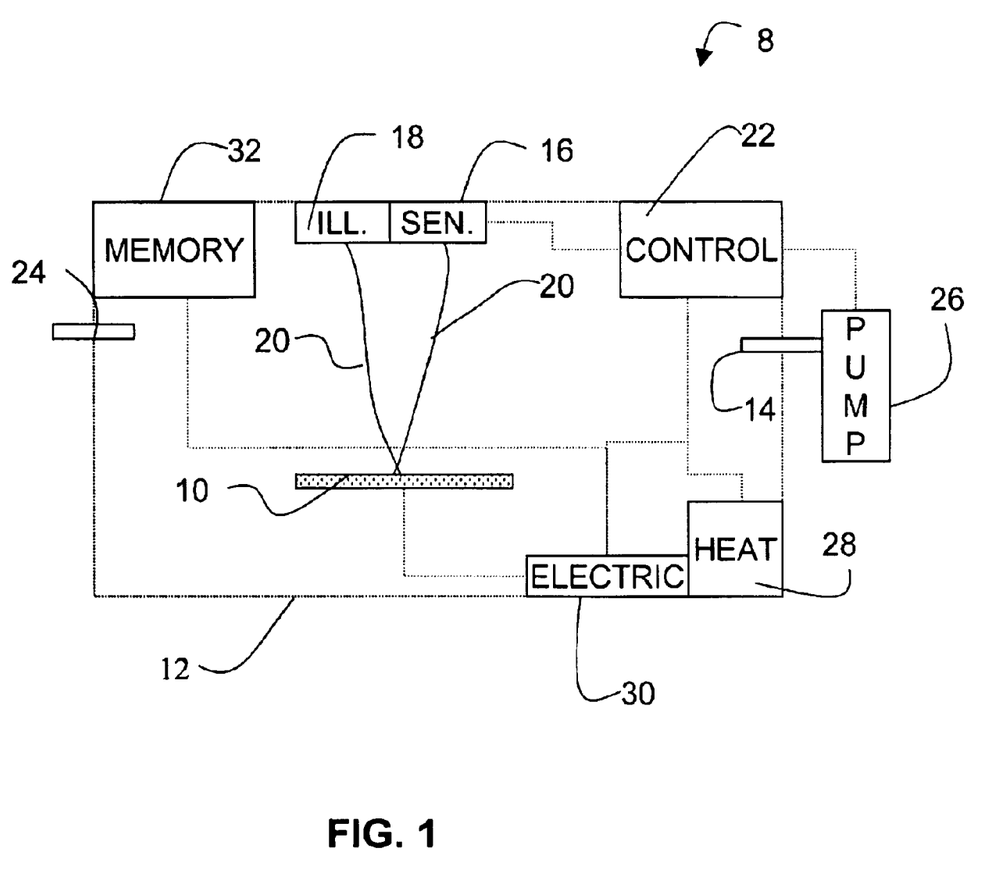
FIG. 1 is a block diagram of a preferred embodiment sample analysis device.

Referring now to FIG. 1, a preferred embodiment sample analysis device 8 is shown. The device includes a porous thin film 10 enclosed in a sample chamber 12. The chamber 12 provides a sealed and controlled environment for analysis. Its construction may vary depending on the setting in which it will be employed, to include, for example, means such as insulation to provide isolation from an external environment. The porous thin film 10 is structured to be stable in the presence of a type of sample to be analyzed, i.e., particular gases or liquids of interest, and to produce time-varying reflectivity at an illumination wavelength as a gas condenses or a liquid diffuses in the pores of the porous thin film 10. The porous thin film 10 may be formed in or on any suitable substrate. A sample introduced into the chamber 12 through an inlet 14 interacts with the pores of the porous thin film 10. As the interaction proceeds, time-varying reflectivity data can be obtained by a light sensor 16 disposed to detect reflections caused by an illumination source 18. The light sensor 16 and illumination source 18 may optically communicate with a surface of the porous thin film 10 via optical fibers 20. The light sensor 16 and illumination source may be within or outside of the chamber 12, so long as an optical path to the porous thin film is provided. Certain types of illumination sources, e.g. semi-conductor lasers, LEDs, etc., are more suitable for a solid state within-chamber arrangement, while others, e.g., a tungsten lamp, are more suited for an outside chamber arrangement.

The light sensor 16 and illumination source 18 are controlled by a controller 22 to cause the light sensor 16 to acquire measured time-varying reflection data from the surface of the porous thin film 10. The controller 22 may acquire the measured time-varying data, and may also control environmental conditions within the chamber 12. For example, the controller 22 might control the inlet 14 and an outlet 24. The controller 22 may also control a pressure pump 26, a heater 28, and/or an electrical stimulator 30 (which can act as a heater). The pressure pump 26, heater 28 or electrical stimulator 30 may be used by the controller 22 to induce a time dependent reflectivity response from a sample resident in the chamber 16 that has been adsorbed into pores in the porous thin film 10. This is useful, for example, to disturb a steady state reached by the sample wherein there would not be a time dependency in measured reflectivity data. In some cases there will be no need for a chamber to create a controlled environment, and the porous thin film 10 can be exposed directly to a sample environment. For example, if the time-varying signal is to be induced by a temperature change (e.g., a heater such as the electrical stimulator 30 attached to the porous thin film), then the sample can be outside of a chamber.

The inlet 14 is controlled by the controller 22 to introduce samples, for example. Similarly, the outlet 24 may be used to evacuate samples, as the interaction of a sample with the pores of the porous thin film 10 may be reversed. The inlet 14 and outlet 24 may be controlled to act in an automated cycle. This may be useful, for example, when the invention is applied to an alarm system, such as a system used to take air samples and initiate an alarm upon detection of a warfare agent, pollutant, toxic gas, or unwanted contaminant in an industrial process. The controller 22 might alternatively comprise part of a laboratory computer or be realized by software in a larger process. The controller 22 might also be a set of signals from other devices, such as a wide scale control system. Detection and analysis may also be initiated by process control software or operator control to conduct a test, such as in a laboratory setting to analyze biological samples or chemical samples, as in drug and biological research. As an additional example, the controller 22 might be realized by signaling and data communication through an interface, such as a short range wireless interface, e.g., bluetooth. The controller, upon making a fit to characteristic data, may produce a signal indicating identification of a sample or an analyte of the sample. For example, an alarm signal could be produced and communicated to another device. Additional example signals include signals used to control or initiate control of another process, or signals used to increment a quantity in memory being used to track detection events.

The controller 22 includes or accesses memory 32 to store measured data, and also to store characteristic data for sample identification. The characteristic data is predetermined to permit identification of analytes of a sample type of interest. The characteristic data may be obtained, for example, experimentally for a class of samples to be analyzed. The characteristic data is representative of time progressive condensation (in the case of a gas) or diffusion (in the case of a liquid) in the pores of the porous thin film 10. The characteristic data is dependent upon the pore size structure and depth, and the rate of condensation of diffusion. The characteristic data permits a fit of measured time-varying reflectivity data from the porous thin film as a sample interacts. A fit of the measured time-varying reflectivity data identifies one or more analytes in the sample being analyzed.

In the case where the porous thin film 10 is a single layer, e.g., a single layer of porous silicon, the relationship between wavelength and intensity of the interference spectrum in reflectivity data follows the Fabry-Pérot interference relationship:

$$n\lambda = \mu L \qquad (1)$$

where $\lambda$ is the wavelength, $\mu$ the refractive index of the porous thin film, n an integer and L the film thickness. The interference fringes depend on porosity and thickness of the porous thin film 10 and on the average refractive index in the pores. The interference fringes shift when the index of refraction of the material changes. Thus, the reflectance spectrum is a sensitive indicator of any molecules that are condensed in the pores. For a given gas, there is a correlation between the pressure and the shift in the fringes. This mechanism is thus reversible versus the pressure and reproducible.

The time response of the porous thin film sensor 10 is fairly considered (wavelength shift of the fringes) to be exponential versus time. Simple fits of the data provide the time constants of condensation or evaporation of gases in the porous structure, which have been found to differ from one compound to another. When the device 8 is exposed to a mixture, the time response becomes multiexponential and the fits give the different time constants of the different constituents. This effect provides a new, easy, rapid and cheap tool for analyzing the composition of gas mixtures. The time variance can be induced by a number of phenomena, such as a pressure pulse, which has been generated by a pump in experiments, and can also be realized by a pulsed heat on the sample by laser irradiation, or by a pulsed voltage applied from one part of the structure to the other, etc. The time response can be measured in many ways, including the exponential fit mentioned above, by time-domain Fourier-transform or by AC frequency analysis methods.

The porous thin film 10 may also comprise a multilayer thin film, such as a porous silicon Bragg reflector. In the case of a Bragg reflector embodiment, the presence of a sample in the pores similarly modifies the average refractive index of the film 10, and a shift of the Bragg peak may be sensed and can be fit to predetermined characteristic data to identify a analyte forming a sample or a part of a sample.

The porous thin film 10 has nanometer scale pores that are small enough to reflect a light wavelength used for illumination of its surface, and may be tailored to suit particular applications of the invention. In accordance with the invention, the pores in the nano-pore structure of the porous thin film 10 act both as separation columns and detectors. Various types of thin films may be used, including for example various porous semiconductor and insulator thin films, with porous silicon representing a preferred embodiment thin film. Certain porous thin films may be suitable for detection of particular gases and liquids and unsuitable for detection of others. Suitability is easily determined by testing the films with the type of gas or liquid to be detected.

Porous Thin Film Preparation and Treatment Method

When silicon is electrochemically corroded in solutions containing hydrofluoric acid, a porous structure results. The pores propagate primarily in the <100> direction of the crystal, and depending on the electrochemical current, the electrolyte composition, and the dopant characteristics of the wafer, the average diameter of the pores can be tuned from a few nanometers to several microns.

Porous silicon samples may be prepared by an electrochemical etch of silicon. A suitable etching solution is prepared by adding an equal volume of pure ethanol to an aqueous solution of HF (48% by weight). Silicon wafers may be cut to size and have specific portions exposed for etching. Electrical contact is made to the wafer to create etching current of sufficient density. To a first approximation, the etching time will determine the thickness of the porous thin film, while the current density controls pore size. Bragg reflectors are produced by modulating the current density periodically during the etch. After etching, porous thin films are rinsed. Porous thin films are preferably oxidized or otherwise chemically modified in an environment selected to immunize the films from being reactive to the types of sample to be tested.

Data Analysis Methods and Experimental Data

Example embodiments of the invention will now be discussed along with experimental data relating to the same. Included in the discussion are preferred embodiments of data analysis methods used by the controller 22 to fit measured data to predetermined characteristic data and to develop characteristic data to be used by the controller 22. Specifications regarding the experimental equipment, measurement techniques and preparation techniques are given primarily so that the obtained experimental data may be fully understood by artisans. Commercial embodiment devices of the invention may take substantially different form, permitting low cost mass manufacturing, for example.

Spectral Measurement

To measure optical interference spectra, we have used an Ocean Optics CCD photodetector, fitted with a fiber optic and lenses to allow detection from small (<1 mm$^2$) sample areas. We used a tungsten lamp as an illumination source. The samples have been mounted in a Schlenk line connected to a solvent reservoir and a Baratron pressure gauge. The porous thin films present relatively long time constants of condensation for gases and diffusion times for liquids. Until an adsorption limit is reached, time dependent reflectivity data may be obtained. The time resolution of the experimental setup is 122 ms (22 ms for the acquisition of one reflectivity spectrum, 100 ms of delay between two successive acquisitions), which is sufficiently lower than the time constants measured (s range).

Porous silicon samples were electrochemically etched from monocrystalline p-type silicon substrates (boron-doped, ~0.001 Xcm, (100) oriented, from Siltronix Inc.), at a current density of 50 mA/cm$^2$, in a 3:1 v/v mixture of aqueous HF (49% hydrofluoric acid) and ethanol. The samples were oxidized in a stream of ozone for 20 minutes prior to mounting in a gas exposure chamber. Fourier transform infrared (FTIR) spectra show that this treatment removes the initial silicon hydride coverage (Si=Hx, with x=1,2,3, stretching bands around 2100 cm±1) and forms silicon oxide (Si=O=Si vibrational band around 1100 cm±1) and some silanol groups (Si=OH vibrational band around 3500 cm±1). This oxidation technique was chosen because of its ability to generate a stable surface. Ozone-oxidized porous silicon samples are stable in air and on exposure to alcohols, esters, ketones and aromatics in both liquid and gas phase. All the experiments we conducted were reversible, indicating that no chemical reaction between the porous thin film and the adsorbed molecules occurs.

After preparation, the porous silicon samples were mounted in a glass chamber connected to the manifold of a Schlenk line that also had a flask of freeze/pump/thaw degassed solvent, a vacuum pump (Leybold Trivac), and a pressure gauge (MKS Baratron) attached. Reflectivity spectra were acquired through the glass window of the sample chamber with a bifurcated optic fiber connected on one end to a tungsten lamp and on the other end to the charge coupled device (CCD) spectrometer. Both illumination of the surface and detection of the reflected light were performed along an axis orthogonal to sample surface.

The typical porous Si thin films used in our experiments had a thickness about 35 µm (measured by profilometry, Dektak II Veeco Sloan Technology), a porosity of about 50% (deduced from the Bruggeman formula) and a refractive index about 1.4 (deduced from the Fourier transform of the reflectivity spectra).

Time-resolved reflectivity experimental data is reflectivity spectra versus time, triggered by a sudden jump in pressure upon analyte introduction, measured with the pressure gauge. The Schlenk line was evacuated to 5 mtorr, and the valve of the degassed solvent flask was then opened. The time necessary to move from the 5 mtorr base pressure to the vapor pressure of the solvent in the flask was found to be between 3 and 6 s. Acquisition of the reflectivity spectra versus time was initiated 2±1 s after the pressure gauge indicated that the pressure was at steady state. All the experiments were performed at room temperature.

Under normal incidence, the constructive interference condition between two waves reflected in a thin film is given by the interference relationship:

$$m\lambda = 2nl \quad (1)$$

where m is the spectral order of the fringe, λ the wavelength, n the refractive index of the film, and l its thickness. Since m is an integer, and since l is constant for a given film, the derivative of Equation 1 is given by:

$$m\Delta\lambda = 2\Delta n l \quad (2)$$

Any modification of the refractive index n will then induce a proportional modification of the interference fringe position λ. When a porous Si film is exposed to analytes in the gas phase, capillary condensation induces an increase of its effective refractive index by replacement of a fraction of air (n=1) by a fraction of liquid (n>1). The position of one fringe was monitored as a function of time after a pulse of analyte vapor was introduced into the sample chamber. Since the data were recorded after the pressure of analyte in the system was at steady state, only diffusion and capillary condensation effects within the porous silicon films determine the temporal response of the data.

Figure 2A:
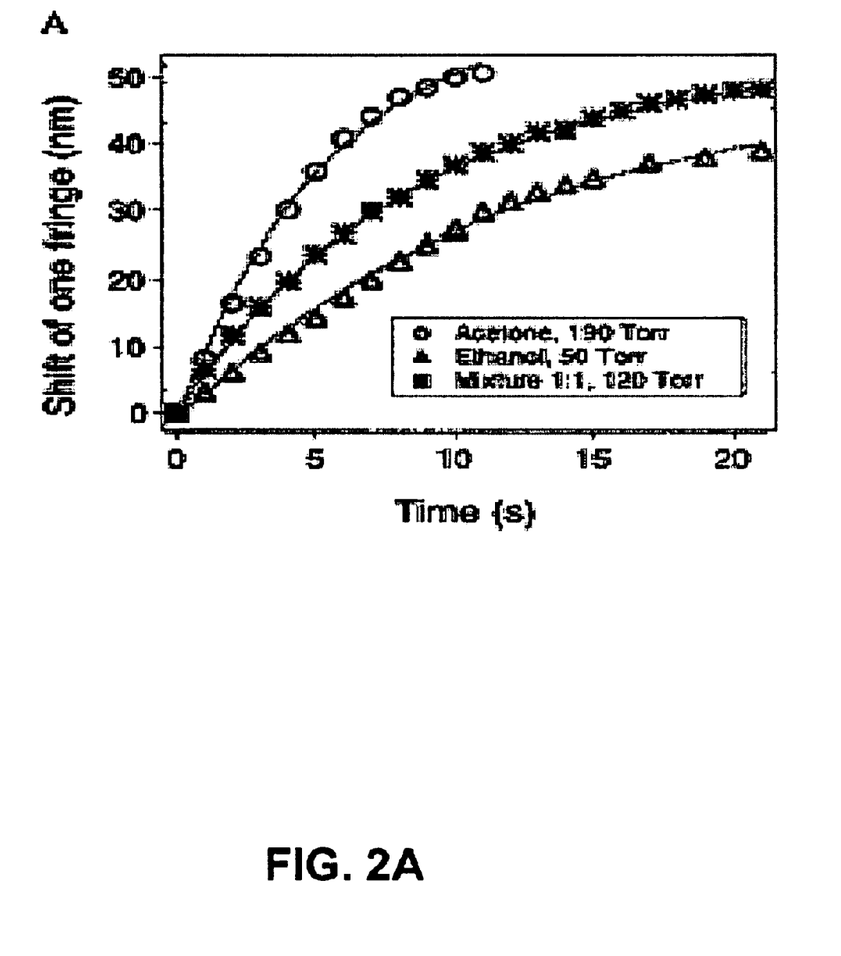
FIGS. 2A and 2B are plots of time-resolved reflectivity data obtained with an experimental embodiment.
Figure 2B:
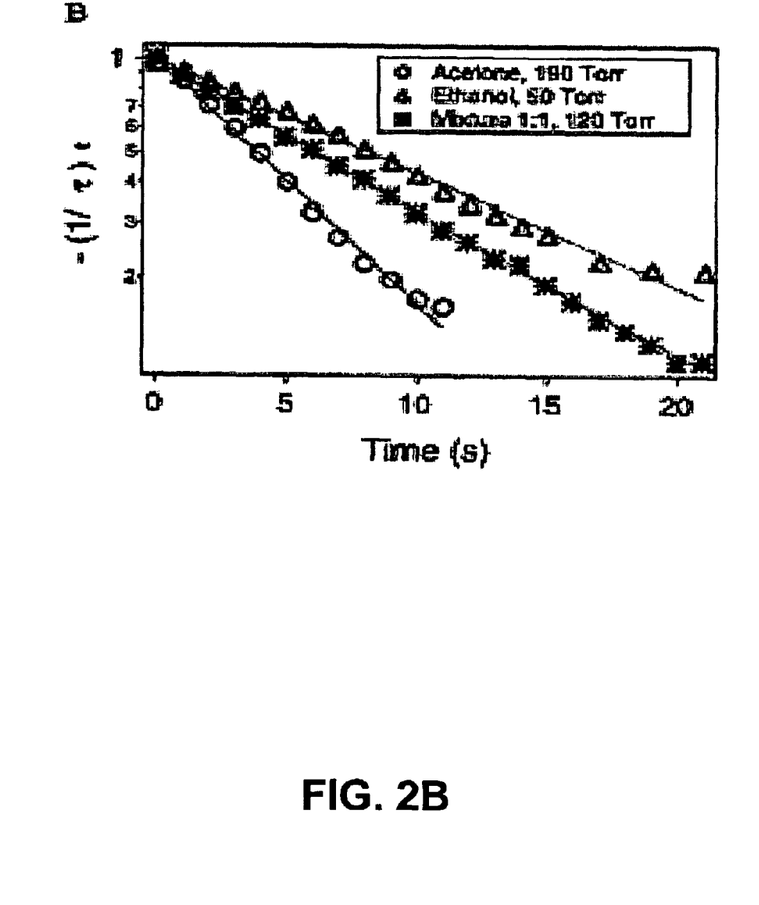

The time-resolved reflectivity spectra of the same porous silicon film after a pulse of pure acetone and pure ethanol are presented in FIG. 2A. Specifically, FIG. 2A is a linear plot of $(\lambda_1-\lambda_0)$ versus time, where λ, is the wavelength of the maximum of an optical fringe at time t and $\lambda_0$ is the wavelength of the fringe maximum at t=0 (before introduction of analyte, approximately 860 nm for all the experiments reported here). The three traces correspond to data for acetone vapor (O), etahol vapor (Δ), and the vapor from a 1:1 (v/v) mixture of acetone/ethanol. The time origin is the time at which the pressure in the Schlenk line reached a stable value. The three spectra were recorded at room temperature on the same porous silicon sample (porosity of 50% and thickness of 35 μm). Markers correspond to experimental points. Dotted lines correspond to single exponential fits. If λ is the position of the fringe at time t, then $\lambda(t)=a+b\exp(-t/r)$, where r is the effective time constant for condensation, a and b are parameters determined by the position of the fringe at t=0 ($\lambda_0$) and at t=equilibrium ($\lambda_{equ}$): $a=\lambda_{equ}$ and $b=\lambda_0-\lambda_{equ}$. The values of the parameters are summarized in Table 1. FIG. 2B is a plot of $(\lambda(t)-a)/b=\exp(-t/r)$. The reflectivity signal reaches steady state a few tens of seconds after the pressure in the system reaches equilibrium. It should be stressed that ethanol and acetone have the same refractive index (n=1.36), but that they have different vapor pressures, 50 torr and 190 torr, respectively. The time required for the system to reach equilibrium is about 10 s for acetone, which has a high vapor pressure, and about 20 s for ethanol, which has a lower vapor pressure. The total amplitude of the red shift in the spectral fringe depends only on the liquid fraction condensed in the sample, since the two compounds have the same refractive index. It is larger for acetone (51±3 nm) than for ethanol (37±3 nm), indicating that more acetone condenses in the pores of these particular samples than does ethanol.

An effective condensation time, s, is defined as the value of the inverse of the slope of a single exponential fit of the wave-length versus time plot. The fits are shown for ethanol and acetone in FIGS. 2A and 2B. The values of s for ethanol and acetone extracted from the fits are 13±2 s and 5±1 s, respectively, demonstrating that the condensation dynamics are different for the two solvents.

The same experiment was performed on the same interferometer (in the same position with respect to the detection optics) but with a 1:1 by volume mixture of acetone and ethanol. The pressure of the ethanol/acetone mixture is 120 torr at 20° C., corresponding to the average of the vapor pressures of the two pure compounds (Raoult's law). The time required to reach equilibrium is about 20 s (FIG. 2A) and corresponds to the time required by the compound with the larger condensation time (ethanol) to diffuse and condense in the porous film. The amplitude of the red shift induced by the mixture (47±3 nm) is intermediate between the shifts induced by the pure compounds (51±3 nm for acetone and 37±3 nm for ethanol), indicating that the filling fraction follows the vapor pressure. A single exponential fit of the time resolved reflectivity spectrum of the mixture leads to a time of condensation of 9±2 s, which is the average of the times of condensation obtained for the pure compounds (these values are summarized in Table 1). A double exponential fit of the time-resolved reflectivity spectrum of the condensation of the mixture gives two different times of condensation: 6±1 s and 12±2 s.

Table 1 lists values of the parameters $\lambda_{equ}-\lambda_0$ and r for the condensation of acetone, ethanol, and of a mixture 1:1 v/v of acetone and ethanol, deduced from the single exponential fits presented in FIGS. 2A and 2B.

TABLE 1

| Analytes | $\lambda_{equ} - \lambda_0$ [nm] | Effective time constant for condensation, r[s] |
|---|---|---|
| acetone | 51 ± 3 | 5 ± 1 |
| ethanol | 37 ± 3 | 13 ± 2 |
| mixture 1:1 | 47 ± 3 | 9 ± 2 |

For a particular porous thin film to be used in a device 8 of the invention, such testing can produce the characteristic data and the data in the table are a form of characteristic data. These values closely match those obtained for the pure compounds (5±1 s and 13±2 s for acetone and ethanol, respectively). The error limits represent the spread of the data obtained by repeating the experiments three times for each analyte. Because the two time constants differ only by a factor of 2, the single exponential curve provides an adequate fit to the time resolved reflectivity spectrum of the mixture. Nevertheless, the correlation factor $\epsilon^2$ is improved by 5% when using a double exponential fit. The results demonstrate that time-resolved reflectivity constitutes a tool to identify solvents and also to analyze binary mixtures, in a process which is analogous to the gas chromatography technique, but with significantly lower resolution.

Figure 3:
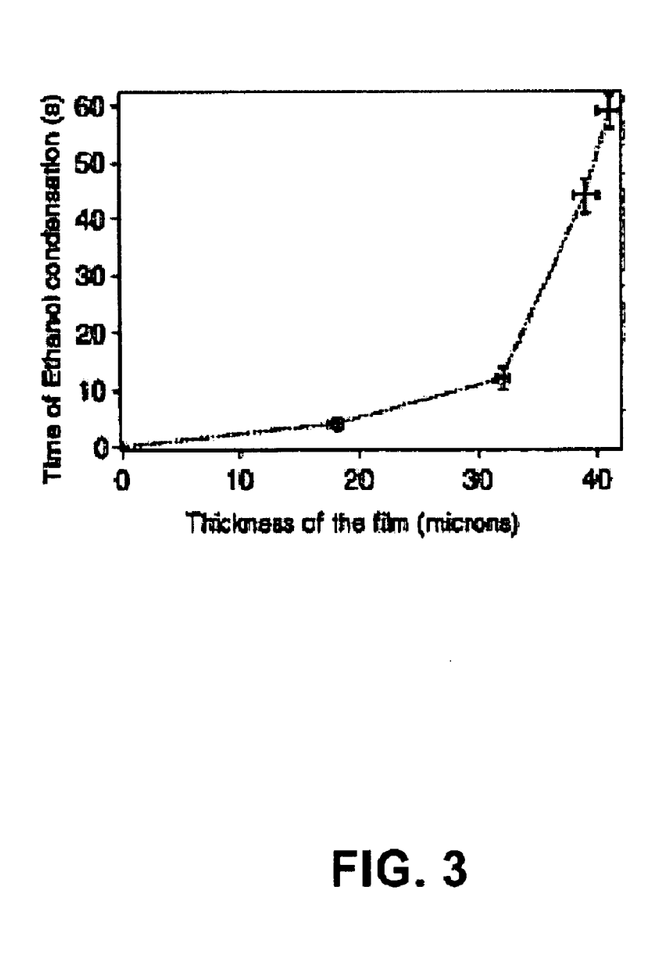
FIG. 3 plots condensation times for ethanol in experimental porous Si films of different thicknesses.

The behavior of the condensation times with the physical properties of the porous silicon thin films was also investigated. FIG. 3 shows the condensation times of ethanol deduced from exponential fits of the time resolved reflectivity spectra for four porous silicon films with different thicknesses. Specifically, FIG. 3 plots the time of condensation of ethanol in the pores, deduced from exponential fits as described in FIGS. 2A and 2B, versus thickness of the porous silicon film, measured by profilometry. The four samples were etched from the same silicon substrate in a solution of saturated (49%) aqueous HF/ethanol 3:1 (v/v) with a current density of 50 mA/cm$^2$ and then oxidized by a 20 min ozone treatment. Markers represent the experimental points with their error bars and the dotted line is included as a guide to the eye. All the porous silicon samples were prepared and oxidized under the same conditions, except for the duration of the etch which was varied from 6 min to 18 min. Thus, the samples had the same porosity, but different thicknesses, ranging from 18 to 41 μm (measured by profilometry). As can be seen in FIG. 3, the condensation time(s) of ethanol increases with film thickness. Such behavior is in qualitative agreement with Fick's law of gas diffusion, which stipulates that the longer the distance, the longer the time of diffusion (mean displacement R is proportional to the square root of the time t: $R=(2D\ t)^{1/2}$, with D being the diffusion coefficient).

Figure 4:
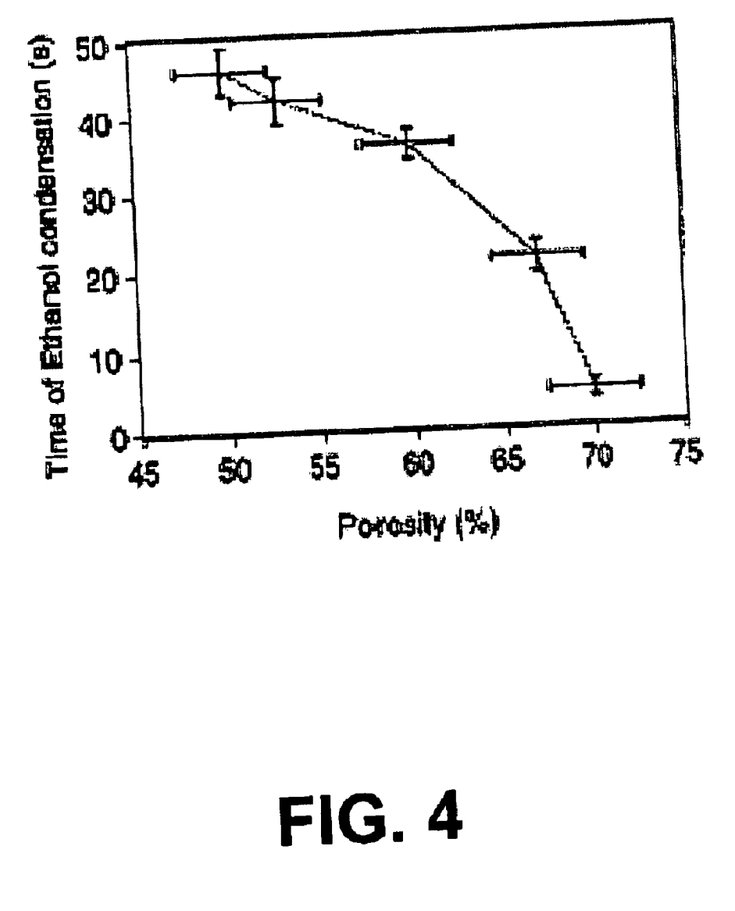
FIG. 4 plots condensation times for ethanol in experimental porous Si films of different porosities.

FIG. 4 shows the condensation times of ethanol deduced from exponential fits of the time resolved reflectivity spectra for five porous silicon films with different porosities. Specifically, FIG. 4 plots the time of condensation of ethanol in the pores, deduced from exponential fits as described in FIGS. 2A and 2B, versus porosity of the porous silicon film. The five samples were etched from the same silicon substrate in a solution of saturated (49%) aqueous HF/ethanol 3:1 (v/v) for 15 min with a current density of 50 mA/cm$^2$. Further dissolution in an aqueous HF solution (25 vol.-%) at open circuit in the dark was performed to increase the pore size. The samples were then oxidized by exposure to a stream of ozone for 20 min. The resulting porous silicon films had porosities between 50% and 70%. The porosity was estimated by the Bruggeman approximation. Markers represent the experimental points with their error bars and the dotted line is included as a guide to the eye. As illustrated in FIG. 4, the condensation time for ethanol decreases with increasing porosity. This result is also in qualitative agreement with the diffusion laws. It should be pointed out that a quantitative analysis should take into account both porosity e and tortuosity q of the porous medium. In this case a new diffusion coefficient D* is defined by D*=(e/q) D. In the above examples, the agreement is only qualitative because various effects such as adsorption, capillary condensation, and chemical interactions between surface and analyte also play a role in the time response of the system.

Time-resolved reflectivity thus constitutes a fast and inexpensive tool to identifying vapors in porous thin films. The components of a binary mixture can be separated temporally in the porous film 10 in a process that is analogous to gas chromatography, where different chemical compounds, with different physical properties and different affinities for the surface of the column are separated by their transit times through the column. Unlike chromatography, the porous thin film 10 plays a dual role of separation column and detector. The behavior of the condensation time of a pure compound versus the physical properties of the porous thin film 10 (like thickness and porosity) qualitatively follows the gas diffusion laws. The pore size, length, and surface derivatization of the porous thin film may be adjusted to optimize specificity. Embodiments of the invention are expected to be especially useful for biological and chemical sensing.

The open pore structure and large specific surface area (a few hundred m$^2$ per cm$^3$, corresponding to about a thousand times the surface of the polished silicon wafer) make porous silicon thin films employed in embodiments of the invention a convenient material for sensitive detection of liquid and gaseous analytes. The ability to electrochemically tune the pore diameters and to chemically modify the surface provides control over the size and type of molecules adsorbed. These properties may be exploited for time resolved reflectivity detection of toxic gases, volatile organic compounds, explosives, DNA, and proteins.

The porous layers generated in the electrochemical etch can be quite smooth, to the extent that the optical interferometers, Bragg filters, and a variety of other high quality optical structures can be generated. The determining physical parameter for reflectivity-based sensor devices is the optical thickness of the films, which is the product of the refractive index (n) and the thickness (L). These are both determined and well controlled by the electrochemical parameters used in the synthesis, and thin films with given optical parameters can be etched in a reproducible way. Characteristic data therefore may be developed for films manufactured in the same manner, without the need to test each individual film that is made.

Devices of the invention are easy and cheap to produce (electrochemical etching of silicon wafers and oxidation processing). They can be used either in continuous reflectivity configuration to measure the pressure of a gas, which would produce a change over time in the measured reflectivity data, or to give the composition of a mixture of different gases. In this latter regard it performs functions of a chromatographic device, with the distinction being that the separation medium used is also the light sensor.

While a specific embodiment of the present invention has been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A method for sample analysis, the method comprising steps of:
   bringing a sample into contact with pores of a porous thin film, the porous thin film having a measurable reflectivity;
   during a period of time-varying reflectivity due to interaction of the sample and the pores, measuring reflectivity over time from the porous thin film; and
   identifying one or more analytes in the sample from a time-varying response in the reflectivity measured over time.

2. The method of claim 1, wherein said step of bringing induces the time-varying reflectivity, and said step of measuring reflectivity is conducted prior to a time when reflectivity reaches a steady state.

3. The method of claim 1, further comprising a step of inducing the period of time-varying reflectivity.

4. The method of claim 3, wherein said step of inducing comprises causing a pressure change in an environment including the sample and the porous thin film.

5. The method of claim 3, wherein said step of inducing comprises heating one or both of the sample and the porous thin film.

6. The method of claim 3, wherein said step of inducing comprises applying electrical stimulation to one or both of the sample and the porous thin film.

7. The method of claim 1, wherein said step of identifying identifies multiple analytes in the sample from the time-varying response in the reflectivity measurements by a fit of the time-varying response to predetermined characteristic time-varying responses.

8. The method of claim 1, wherein said step of identifying comprises determining a time constant of the time-varying response and matching the time constant to a time constant from a predetermined characteristic set of time constants.

9. The method of claim 8, wherein the time constant is defined as $\tau$ and is determined according to the following:

$$\lambda(t) = a + b^{(-1/\tau)}$$

wherein $\lambda(t)$ is the position of a shift of an interference fringe in measured reflectivity at time t, a is the position of an interference fringe at an equilibrium of reflectivity when the sample contacts the porous thin film, and b is the difference between a position of an interference fringe at an equilibrium of reflectivity when the sample contacts the porous thin film and a position of an interference fringe at a time when the sample initially contacts the porous thin film.

10. The method of claim 1, wherein said step of identifying comprises determining an effective interaction time of the sample and the pores from the time-varying response, the effective interaction time being defined as the inverse of a slope of a single exponential fit of an interference fringe wavelength shift versus time plot.

11. The method of claim 10, wherein the effective interaction time comprises an effective condensation time of a gas sample.

12. The method of claim 10, wherein the effective interaction time comprises an effective diffusion time of a liquid sample.

13. The method of claim 10, wherein an analyte is identified by comparing the effective interaction time to predetermined characteristic effective interaction times.

14. The method of claim 1, wherein said step of identifying comprises determining an effective interaction time of the sample and the pores from the time-varying response, the effective interaction time being defined as the inverse of a slope of a double exponential fit of an interference fringe wavelength shift versus time plot.

15. The method of claim 14, wherein the effective interaction time comprises an effective condensation time of a gas sample.

16. The method of claim 14, wherein the effective interaction time comprises an effective diffusion time of a liquid sample.

17. The method of claim 14, wherein an analyte is determined by comparing the effective interaction time to predetermined characteristic effective interaction times.

18. The method of claim 1, wherein the porous thin film comprises oxidized porous silicon.

19. The method of claim 1, wherein the porous thin film comprises a single layer porous thin film and said step of identifying comprises determining one or both of a change in intensity and wavelength of Fabry-Pérot interference fringes in the time-varying response.

20. The method of claim 1, wherein the porous thin film comprises a Bragg reflector and said step of identifying comprises detecting a Bragg peak shift in the time-varying response.

21. A method for analyzing a gaseous or liquid sample, comprising condensing or diffusing the sample in pores of a porous thin film, measuring a time-varying response of reflectivity intensity and wavelength with respect to a surface of the porous thin film, and identifying at least one analyte in the sample based upon the time-varying response.

22. The method of claim 21, wherein said step of identifying comprises a fit of the time-varying response to predetermined characteristic time-varying responses.

23. The method of claim 21, further comprising a step of inducing the time-varying response.

24. The method of claim 23, wherein said step of inducing comprises altering pressure of an environment including the porous thin film and the sample.

25. The method of claim 23 wherein said step of inducing comprises heating one or both of the porous thin film and the sample.

26. The method of claim 23, wherein said step of inducing comprises electrically stimulating one or both of the porous thin film and the sample.

27. The method of claim 21, wherein said step of identifying comprises determining an effective interaction time of the sample and the pores from the time-varying response, the effective interaction time being defined as the inverse of a slope of a single exponential fit of an interference fringe wavelength shift versus time plot.

28. The method of claim 27, wherein the effective interaction time comprises an effective condensation time of a gas sample.

29. The method of claim 27, wherein the effective interaction time comprises an effective diffusion time of a liquid sample.

30. The method of claim 27, wherein an analyte is determined by comparing the effective interaction time to predetermined characteristic effective interaction times.

31. The method of claim 21, wherein said step of identifying comprises determining an effective interaction time of the sample and the pores from the time-varying response, the effective interaction time being defined as the inverse of a slope of a double exponential fit of an interference fringe wavelength shift versus time plot.

32. The method of claim 31, wherein the effective interaction time comprises an effective condensation time of a gas sample.

33. The method of claim 31, wherein the effective interaction time comprises an effective diffusion time of a liquid sample.

34. The method of claim 21, wherein the porous thin film comprises a single layer porous thin film and said step of identifying comprises determining one or both of a change in intensity and wavelength of Fabry-Pérot interference fringes from the time-varying response.

35. The method of claim 21, wherein the porous thin film comprises a Bragg reflector and said step of identifying comprises detecting a Bragg peak shift from the time-varying response.

36. A method for analyzing a gaseous or liquid sample, the method comprising steps of:
   determining a change in reflectivity data from measured reflectivity of the sample while the sample is condensed or diffused into pores of a porous thin film;
   fitting the change in reflectivity data to predetermined characteristic patterns to identify an analyte of the sample.

37. A sample analysis device, the device comprising:
   a porous thin film;
   means for introducing a liquid or gaseous sample into pores of the porous thin film the sample chamber;
   means for acquiring time-varying reflectivity data with respect to a surface of the porous thin film; and
   means for determining an analyte from the sample based upon the time-varying reflectivity data.

38. The device of claim 37, wherein said porous thin film comprises oxidized porous silicon.

39. The device of claim 37, wherein said porous thin film comprises a porous structure tailored to diffuse or condense a molecule type of interest.

40. The device of claim 39, wherein said molecule type of interest comprises a toxic gas.

41. The device of claim 39, wherein said molecule type of interest comprises a solvent.

42. The device of claim 39, Wherein said molecule type of interest comprises an explosive.

43. The device of claim 39, wherein said molecule type of interest comprises a nucleic acid.

44. The device of claim 39, wherein said molecule type of interest comprises a protein.

45. The device of claim 37, further comprising means for inducing a time-varying reflectance response.

46. The device of claim 37, wherein the porous thin film is within a sample chamber and said means for inducing comprises a pump to control the pressure in said sample chamber.

47. The device of claim 46, wherein said means for inducing comprises means for heating one or both of said porous thin film and the sample.

48. The device of claim 46, wherein said means for inducing comprises means for electrically stimulating one or both of said porous thin film and the sample.

49. The device of claim 37, wherein said porous thin film comprises a single layer porous thin film and said means for determining determines one or both of a change in intensity and wavelength of Fabry-Pérot interference fringes in the time-varying reflectivity data.

50. The device of claim 37, wherein said porous thin film comprises a Bragg reflector and said means for determining determines a Bragg peak shift in the time-varying reflectivity data.

51. A sample analysis device, the device comprising:
a porous thin film;
a sample chamber enclosing said porous thin film including an inlet to accept a gas or liquid sample for interaction with said porous thin film;
an illumination source disposed to illuminate a surface of the porous thin film;
a light sensor to detect reflections from the surface of the porous thin film; and
a controller that controls said illumination source and said light sensor to acquire measured time-varying reflection data from the surface of the porous thin film and to fit the measured time-varying reflection data to predetermined characteristic time-varying reflection data.

52. The device of claim 51, further comprising an outlet for said sample chamber.

53. The device of claim 52, wherein said controller controls the outlet and the inlet and operates automatically to periodically acquire measured time-varying reflection data from the surface of the porous thin film and to fit the measured time-varying reflection data to the predetermined characteristic time-varying reflection data.

54. The device of claim 53, wherein said controller produces a signal when a fit is made to the predetermined characteristic time-varying reflection data.

55. The device of claim 51, wherein said porous thin film comprises a single layer porous thin film, and the characteristic time-varying reflection data comprises one or both of intensity and wavelength data for Fabry-Pérot interference fringe shifts characteristic of predetermined analytes.

56. The device of claim 51, wherein said porous thin film comprises a Bragg reflector, and the characteristic time-varying reflection data comprises Bragg peak shifts characteristic of predetermined analytes.

* * * * *

UNITED STATES PATENT AND TRADEMARK OFFICE
CERTIFICATE OF CORRECTION

PATENT NO. : 7,042,570 B2  Page 1 of 1
APPLICATION NO. : 10/339163
DATED : May 9, 2006
INVENTOR(S) : Sailor et al.

It is certified that error appears in the above-identified patent and that said Letters Patent is hereby corrected as shown below:

Column 7, line 27, after "where" please delete "$\lambda$," and insert -- $\lambda_1$ -- therefor.

Signed and Sealed this

Eighth Day of August, 2006

JON W. DUDAS
*Director of the United States Patent and Trademark Office*